United States Patent [19]

Rosano

[11] 4,146,499

[45] Mar. 27, 1979

[54] METHOD FOR PREPARING MICROEMULSIONS

[76] Inventor: Henri L. Rosano, 848 Woodland Ave., Oradell, N.J. 07649

[21] Appl. No.: 818,965

[22] Filed: Jul. 25, 1977

Related U.S. Application Data

[63] Continuation-in-part of Ser. No. 721,448, Sep. 18, 1976, abandoned.

[51] Int. Cl.$^2$ ............................................. B01J 13/02
[52] U.S. Cl. ............................. 252/186; 252/187 H; 252/8.55 D; 252/311; 252/312; 252/364; 166/274; 166/275
[58] Field of Search ................... 252/186, 187 H, 311, 252/312, 8.55 D, 364, DIG. 9; 166/274, 275

[56] References Cited

U.S. PATENT DOCUMENTS

| | | | |
|---|---|---|---|
| 3,467,194 | 9/1969 | Kinney et al. | 166/305 R |
| 3,493,048 | 2/1970 | Jones | 166/275 |
| 3,506,070 | 4/1970 | Jones | 166/273 |
| 3,778,381 | 12/1973 | Rosano et al. | 252/311 |
| 3,813,345 | 5/1974 | Urton | 252/312 |

OTHER PUBLICATIONS

Gerbacia et al., J. Am. Oil Chem. Soc., vol. 53, No. 3, pp. 101–104 (1976).

*Primary Examiner*—Benjamin R. Padgett
*Assistant Examiner*—Irwin Gluck
*Attorney, Agent, or Firm*—Brumbaugh, Graves, Donohue & Raymond

[57] ABSTRACT

A unique method for the preparation of oil-in-water microemulsions is described. In carrying out this method, microemulsions are prepared in a four-step process: (1) a surfactant is selected which is just barely soluble in the oil phase; (2) the surfactant thus selected is dissolved in the oil to be emulsified in an amount effective to yield a fine emulsion of the emulsified oil in an aqueous phase; and (3) the oil, together with its dissolved surfactant, is added to the water phase and shaken or stirred; and (4) finally, there is provided a second surfactant in the water phase which is somewhat more soluble in water than the first surfactant to produce a substantially clear microemulsion of oil in water.

46 Claims, No Drawings

METHOD FOR PREPARING MICROEMULSIONS

This is a continuation-in-part of my co-ending application, Ser. No. 721,448, filed Sept. 18, 1976, now abandoned.

This invention relates to microemulsions. More particularly, it relates to the preparation of oil-in-water microemulsions.

Microemulsions have heretofore been known in which water or various compositions of an essentially aqueous nature are dispersed in an oil phase. However, there has been only limited success in preparing microemulsions of an essentially lipophilic phase dispersed in water. One such example of an oil-in-water microemulsion is set forth in my prior U.S. Pat. No. 3,778,381. The aforementioned prior patent describes the preparation of microemulsions of droplets of certain fluorinated organic compounds dispersed throughout an aqueous system.

A microemulsion is a dispersion of two immiscible liquids (one liquid phase being "dispersed" and the other being "continuous") in which the individual droplets of the dispersed phase have an average radius less than about ¼ of the wavelength of light. Typically, in a microemulsion the dispersed phase droplets are less than about 1,400Å radius, and preferably in the order of 100Å to 500Å.

The basic principles of preparing microemulsions of water or other aqueous systems dispersed in oil are generally well known. Typically, oil, water and a primary surfactant are mixed together to form a lactescent emulsion. The lactescent emulsion is titrated with a secondary surfactant (or cosurfactant) until the mixture becomes clear. By way of illustration, a microemulsion may be prepared by emulsifying 5 ml of water in 25 ml n-hexadecane employing 0.287 gms of sodium lauryl sulfate to form a milky emulsion. The mixture is then titrated with 1-pentanol until clarity is achieved. 1-pentanol is not too soluble in either oil or in water, and is an efficient cosurfactant with this system.

The basic theory of microemulsions is more fully described in my publication in the Journal of Society of Cosmetic Chemists, v. 25, pp. 609–619 (November, 1974). Prior to 1972, microemulsions had generally been thought to be thermodynamically stable systems of droplets of a dispersed liquid in a continuous liquid phase, the two liquids being immiscible. Those skilled in the art had believed that the formation of microemulsions required only that the proper thermodynamic conditions be realized. However, the formation of practical microemulsions continued to be unpredictable.

In 1973, Gerbacia and Rosano, Journal of Colloid and Interface Science, v. 44, pp. 242–248, showed that transport phenomena were significant in the preparation of microemulsions. Tests were made on the interfacial tension of the n-hexadecane/water system employing sodium dodecyl sulfate (SDS) as a primary surfactant and 1-pentanol as a secondary surfactant. The tests showed that under equilibrium conditions the system has a positive interfacial tension. However, when pentanol was injected into either the oil or the water phase of a two-phase mixture of oil and water containing SDS and the pentanol was allowed to distribute between them, the interfacial tension would drop for a period of time and then rise to an equilibrium value. From this, as well as certain other evidence, it was deduced that the formation of a microemulsion was not dependent upon simple thermodynamic stability but, to the contrary, dependent at least in part upon the occurrence of kinetic conditions favorable to the dispersion of the dispersed phase into a microemulsion.

The dependence of microemulsification on kinetic conditions was demonstrated using separate water and hexadecane solutions containing SDS and pentanol. Solutions of SDS and pentanol in oil and in water were separately prepared, each containing the equilibrium amount of pentanol that would be present in the final microemulsion. The equilibrium concentrations had previously been determined for this system. The two solutions were then mixed together for approximately 20 minutes at 30° C. but no microemulsion resulted. Had the components been combined as described above (i.e., by titration with alcohol), a microemulsion would have resulted readily. The preparation of microemulsions by titration allows transport of the amphiphatic component through the interface to occur.

As already indicated, only limited success has been had in formulating oil-in-water microemulsions. The formation of oil-in-water microemulsions has now been found to require selection of primary and secondary surfactants having the correct solubility relationships with respect to the oil and water systems and with respect to each other, proper selection of the order in which the various ingredients are combined and requires that before titration with a secondary solvent is undertaken the oil-in-water system must first be converted into a finely divided lactescent emulsion.

The primary surfactant is an amphiphatic molecule (more fully described below) adsorbed at the oil-water interface. By "amphiphatic", I am referring to typical surfactants having a double affinity, i.e., a portion of the molecule which is hydrophilic and a portion which is lipophilic. In an optimum emulsion (including microemulsions), the amount of primary surfactant is just sufficient to form a monomolecular interfacial layer between the dispersed phase and the continuous phase. If a given volume, V, of a "dispersed" phase liquid is broken into spherical droplets of radius r, the total volume of the dispersed phase is equal to:

$$V = a \times (4/3)\pi r^3, \text{ and}$$

the surface area of the droplets is:

$$A = a \times 4\pi r^2.$$

Assuming that the surface area of the droplets is covered by a monomolecular layer of n atoms of surfactant, each atom having a cross-sectional area of $\sigma$ (i.e., $A = n \times \sigma$); for a given volume of dispersed phase, amount of surfactant and size of the surfactant molecule, the theoretical diameter of an individual dispersed droplet is given by the equation:

$$r = 3V/n \times \sigma \tag{1}$$

In the foregoing equations:
 a = the total number of droplets of the dispersed phase;
 r = the radius of an individual droplet of the dispersed phase;
 n = the number of surfactant molecules;
 $\sigma$ = the cross sectional area occupied by a surfactant molecule at the oil-water interface;
 A = the total surface area of the dispersed phase; and
 V = the total volume of the dispersed phase.

In accordance with the present invention, a process has now been found for preparing microemulsions of a water-immiscible liquid in an essentially aqueous phase. For brevity in the following description, these will be referred to as oil and water phases, although it should be understood that this is without intent to limit the disclosure to specific water-immiscible liquids, or to a water phase containing no other ingredients. The process comprises four basic steps:

1. An amphiphatic surfactant, herein referred to as the primary surfactant, is selected having a hydrophilic-lipophilic balance (herein HLB) not substantially less than required to make the primary surfactant soluble in the oil phase. The HLB depends upon the relative size and strength of the hydrophilic and lipophilic moieties of the amphiphatic surfactant (i.e., relatively lipophilic will be soluble in the oil while surfactants of a high HLB will be insoluble).

Solubility may be determined by a simple test. A fraction of a gram of surfactant is added to several milliliters of oil. If the surfactant is insoluble, a cloudy suspension will result; if it is soluble the solution will be clear. Using the simple test, a compound will be selected in which thw HLB is just low enough to render the compound soluble.

2. A solution of the primary surfactant selected in the first step is prepared in the oil which is to become the oil phase. That solution should contain sufficient primary surfactant to form an essentially monomolecular layer of surfactant on the dispersed oil phase droplets after the oil has been dispersed as a microemulsion. If the formula I above is used to estimate the amount of primary surfactant to be employed, allowance should be made not only for the primary surfactant actually adsorbed at the oil-water interface but also for some additional primary surfactant which may be distributed between the oil and water phases. In the absence of a secondary surfactant as hereinafter described, the primary surfactant at this stage of the process should be capable of producing a finely-dispersed emulsion of the oil in the water. Typically, the oil will contain approximately 20% by volume of the primary surfactant but may contain as little as 10% of the primary surfactant.

3. After dissolving the primary surfactant in the oil, the oil is then dispersed in the aqueous phase. If necessary, mild agitation may be provided to insure thorough dispersion. At this point, the resulting emulsion is a finely-dispersed oil-in-water emulsion usually appearing as a milky, or lactescent dispersion.

4. Finally, a secondary surfactant (or cosurfactant) is provided in the aqueous phase to convert the lactescent dispersion into a microemulsion. In this step, the lactescent dispersion prepared in the third step may be titrated with a secondary surfactant or cosurfactant. In the alternative, a secondary surfactant may be dissolved in the aqueous phase prior to dispersion. Generally the cosurfactant has a lower HLB than the primary surfactant selected in the first step. The cosurfactant may be selected from the same general series of compounds as the primary surfactant, but it is not necessary to do so and, as will be apparent from the further description of my invention below, the cosurfactant may not be chemically related to the primary surfactant.

The foregoing process is generally applicable to dispersion of hydrophobic oils and solvents in an aqueous phase, and is also of value in the preparation of dispersions of a variety of hydrophobic substances such as solids, semi-solids or oils which may be dissolved in the solvent. The use of a volatile solvent is particularly useful where the hydrophobic substance is a solid, semi-solid or oil not readily dispersed in an aqueous medium even with the provision of surface-active dispersing agents. In accordance with this further embodiment of the present invention, a solution of such a hydrophobic solid, semi-solid or oil is prepared employing a water-immiscible fluid solvent such as light mineral oil, a lower boiling hydrocarbon, an oxygenated hydrocarbon, or a halogenated hydrocarbon. These solvents may be used alone or in mixtures. After the solution of the inorganic solid or semi-solid to be dispersed in a suitable solvent has been prepared, the solution is then treated as the "oil" phase in accordance with the process of the present invention, wherein an appropriate primary surfactant is identified and dissolved in the solution of the hydrophobic substance to be dispersed. The completed solution is dispersed in the aqueous phase to form a lactescent emulsion, and the lactescent emulsion is converted to a microemulsion with a cosurfactant.

Dispersions of hydrophobic substances prepared in the foregoing manner may be employed as is, or may be further treated to remove the solvent if it is desired to have a finished product containing the hydrophobic substance dispersed in water free from intermediate solvent. Where the solvent is to be removed, the solvent should have a sufficient volatility that it can be removed from the aqueous system by evaporation. Typically, therefore, for this purpose solvents will have a boiling point below about 85° C. and preferably below about 75° C. Removal of the solvent results in a micro-dispersion of the hydrophobic solid, semi-solid or oil maintained by the mixed primary surfactant-secondary surfactant system.

Microemulsions prepared in accordance with the present invention have many advantages. In a process or composition where a dispersion of a hydrophobic substance is employed, it usually has been necessary to provide substantial mechanical work if such a hydrophobic substance is to be dispersed in an aqueous system. Consequently, non-aqueous liquid vehicles have frequently been employed to carry these substances in liquid systems.

For instance, chemical reactions involving hydrophobic substances in liquid systems have heretofore required liquids other than water as a reaction vehicle since the hydrophobic substance would precipitate rapidly or separate from an aqueous phase. This poses obvious disadvantages, economic as well as safety. If the lipophilic reactant is not well dispersed, control of the reaction can be difficult, as the addition of the substance to the other reaction systems may result in immediate reaction, with undesired temperature changes, side reactions, or both. The present invention provides a convenient means of preparing microdispersions of such substances in water to facilitate chemical reactions and other uses of such substances.

Many drugs are also hydrophobic in nature, and this requires that the drugs be sold or dispensed in tablet form for oral administration. Preparation of such drugs in liquid form would require a liquid vehicle other than water, which is not desirable for oral administration. Similarly, the hydrophobic nature of a drug can limit its use for intravenous injection. Preparation of microemulsions of such drugs in accordance with the present invention may aid in overcoming these disadvantages.

Still other examples of hydrophobic substances to which the present invention may be applied are foods such as peanut oil or corn oil which must be consumed as part of an edible substrate since the oils are not compatible with water and it has been heretofore impractical to form stable dispersions of such materials in an aqueous medium.

Often hydrophobic substances such as water-insoluble dyes and pigments must be employed in liquid vehicles other than water due to the difficulty of dispersing them in an aqueous medium. These non-aqueous systems present further problems when disposing of them in ordinary sewage systems. Such substances also can be advantageously used as microemulsions.

Other hydrophobic substances which may be used in accordance with the present invention are light mineral oils or mixtures of light mineral oils with substances such as lanolin, fluorocarbons and silicones such as dimethyl siloxanes, natural waxes, synthetic waxes (such as polyethylene wax), fabric and hair conditioners. Such microemulsions have particular value in various cosmetics to provide skin emolients. Microemulsions having such emolients may also be employed in shampoos, shaving creams, hand soaps, etc.

From the foregoing, it is apparent that a wide variety of hydrophobic substances may find utility as stable dispersions in accordance with the present invention. Included among these are hydrophobic substances which may be liquid, semi-solid or solid, dye stuffs, pigments, hydrophobic polymers, natural and synthetic waxes, drugs and pharmaceutical preparations, foods containing edible fats, waxes or oils such as mono-, di- and tri-glycerides and free fatty acids which are insoluble or immiscible in water. Other chemicals to which the present invention is applicable are long-chain fatty alcohols, vegetable and mineral oils, waxes, greases and the like.

Where the hydrophobic substance must be dissolved in a solvent to form the "oil" of the oil-in-water emulsion, the solvent should be insoluble in water or, at most, only slightly soluble. In those modifications of the present invention where it is desired to remove the solvent, it is preferred that the solvent approach total insolubility and have a boiling point below about 85° C. Among solvents useful in the process of this invention are low boiling hydrocarbons such as hexane, benzene, toluene, xylene, mineral spirits, petroleum ethers and other similar hydrocarbons. Halocarbons may also be employed, preferably having 1-3 carbon atoms and substituted by chlorine, fluorine (or both) and possibly containing a hydroxyl group (e.g., halo-alcohols), such as carbon tetrachloride chloroform, dichloromethane, ethyl chloride, dichloroethane, trichlorotrifluoroethane, dichlorotrifluoroethane, dichlorodifluoroethane, dichlorofluoroethane, monochlorodifluoroethane, and the like. Still other examples of oil phase substances are the water-immiscible oxygenated hydrocarbons such as the higher molecular weight acids, esters, ketones or alcohols. Specific examples include 1-pentanol, diethylether, etc. For many purposes the halocarbons as solvents are preferred in view of their ability to dissolve most hydrophobic substances and the ease with which they are removed from the aqueous system. From a practical point of view, the solvent will contain at least 5% of the hydrophobic substances; however, the invention is not limited to such systems. In some cases, the solvent will comprise a dominant portion of the oil phase at least at the time of microemulsification. In this respect, a "dominant portion" is an amount of solvent such that the microemulsification characteristics of the solvent system with the dissolved substances therein are generally those of the solvent. In other cases, the solvent may affect the lipophilic characteristics of the oil phase sufficiently to alter the HLB required of the primary surfactant.

It should be recognized that the basic requirements placed on the water-immiscible solvent used in the process of the present invention is that it be a solvent for, or miscible with, the hydrophobic substance to be dispersed, that it be emulsifiable with water, and that it not affect the substance to be dispersed. As noted above, where the solvent is to be removed it, of course, must also be relatively more volatile than the water.

In carrying out the process of the present invention, the selection of the primary surfactant is of considerable importance.

There are a great many surfactants, anionic, cationic, non-ionic or amphoteric in character, which may be employed, depending upon the hydrophobic substance to be employed. Among the well-known surfactants useful in the process of the present invention are the sorbitan esters of fatty acids having 10 to 22 carbon atoms; polyoxyethylene sorbitan esters of $C_{10}$ to $C_{22}$ fatty acids having up to 80% ethylene oxide; polyoxyethylene sorbitol esters of $C_{10}$ to $C_{22}$ fatty acids, polyoxyethylene derivatives of fatty phenols having 6 to 20 carbon atoms and up to 80% ethylene oxide; fatty amino and amido betaines having 10 to 22 carbon atoms; fatty alcohols of 5 to 16 carbon atoms, polyoxyethylene condensates of $C_{10}$ to $C_{22}$ fatty acids or fatty alcohols having up to 80% ethylene oxide; polyoxyethylene-polyoxypropylene block polymers; ionic surfactants such as the alkylaryl sulfonates of 6 to 20 carbons in the alkyl group; $C_{10}$ to $C_{22}$ fatty acid soaps; $C_{10}$ to $C_{22}$ fatty sulfates; $C_{10}$ to $C_{22}$ alkyl sulfonates; $C_{10}$ to $C_{22}$ fatty amine oxides; fatty imidazolines of $C_6$ to $C_{20}$ carbon atoms; fatty amido sulfobetaines having 10 to 22 carbon atoms; quaternary surfactants such as the fatty ammonium compounds having 10 to 22 carbon atoms; $C_{10}$ to $C_{22}$ fatty morpholine oxides, alkali metal salts of carboxylated ethoxylated $C_{10}$ to $C_{22}$ alcohols having up to 80% E.O., ethylene oxide condensates of $C_{10}$-$C_{22}$ fatty acid monoesters of glycerins having up to 80% E.O. and the mono- or diethanol amides of $C_{10}$ to $C_{22}$ fatty acids, etc. As is well known in the field of surfactants, the counter ion in the case of anionic surfactants may be any of the alkali metals, ammonia, or substituted ammonias such as trimethylamine or triethanol amine. Usually ammonium, sodium and potassium are preferred. In the case of cationic surfactants, the counter ion is usually a halide, sulfate or methosulfate, the chlorides being the most common industrially available compounds. The foregoing compounds have been described with particular reference to fatty derivatives. It is the fatty moiety usually forming the lipophilic moiety. A common fatty groups is an alkyl group of natural or synthetic origin. In most instances, the alkyl group may be replaced by the corresponding ethyleneically saturated group having one or more ethylene linkages such as commonly occur in nature. Common unsaturated groups are oleyl, linoleyl, decenyl, hexadecenyl, dodecenyl, etc. In appropriate cases, as known in the art, the alkyl group may be cyclic, i.e., cycloalkyls, or may be straight or branched chain.

Among the surfactants found particularly useful in accordance with the present invention are nonylphenol-polyoxyethylene condensates, the sorbitan and sorbital mono esters $C_{12}$ to $C_{18}$; fatty acids, and their ethylene oxide condensates.

Other representative primary surfactants are: sorbitol monolaurate-ethylene oxide condensates; sorbitol monomyristate-ethylene oxide condensates; sorbitol monostearate-ethylene oxide condensates; dodecylphenol-ethylene oxide condensates; myristylphenol-ethylene oxide condensates; octylphenyl-ethylene oxide condensates; stearylphenol-ethylene oxide condensates; lauryl alcohol-ethylene oxide condensates; stearyl alcohol-ethylene oxide condensates; secondary alcohol-ethylene oxide condensates such as commercial $C_{14}$-$C_{15}$ secondary alcohols condensed with ethylene oxide (commercially available as "Tergitol"); decyl amino betaine; coco amino betaine; cetyl amino betaine; coco amido betaine; coco amido sulfobetaine; oleyl amido betaine, coco imidazoline; coco sulfoimidazoline, cetyl imidazoline, 1-hydroxyethyl-2-heptadecenyl imidazoline; 1-hydroxyethyl-2-mixed heptadecenyl heptadecadienyl imidazoline; n-coco morpholine oxide; decyl dimethyl amine oxide; coco amido dimethyl amine oxide; sorbitan tristearate condensed with ethylene oxide; sorbitan trioleate condensed with ethylene oxide; sorbitan trioleate; sodium or potassium dodecyl sulfate; sodium or potassium stearyl sulfate; sodium or potassium dodecyl benzene sulfonate; sodium or potassium stearyl sulfonate; triethanol amine salt of dodecyl sulfate; trimethyl dodecyl ammonium chloride; trimethyl stearyl ammonium methosulfate; polyoxyethylene/polyoxypropylene block polymers having 10% –80% ethylene oxide (by weight) and a molecular weight of 900 to 16,000; sodium laurate; sodium or potassium myristate; and sodium or potassium stearate.

As noted above, in carrying out the present invention it is desired to select a primary surfactant from a series of surfactants of varying hydrophilic-lipophilic balance (HLB). The HLB should be such that the surfactant will produce a fine lactescent emulsion. Usually, the HLB balance will be not substantially less than required to make the primary surfactant soluble in the oil phase using the simple test described below.

The polyoxyethylene condensates are particularly convenient in this respect because the HLB of the polyoxyethylene surfactants can be made to vary in a regular fashion depending upon the amount of ethylene oxide condensed onto the hydrophilic portion of the molecule. This facilitates the selection of a primary surfactant having the correct HLB.

While the use of a single surfactant can, in many instances, be sufficient to serve as the primary surfactant in accordance with the process of this invention, the use of a mixed primary surfactant may prove advantageous. By way of illustration, when selecting a primary or secondary surfactant from a series of polyoxyethylene condensates of nonylphenol, the commercially available condensates may contain, for example, 1, 4 or 9 ethylene oxide units condensed with the nonylphenol. In such a sequence of compounds, a mixture of one part of nonylphenol-4EO and 1 part nonylphenol-9EO may prove more effective as the primary surfactant than either nonylphenol-4EO or nonylphenol-9EO alone.

As indicated above, the suitability for the primary surfactant for any given oil phase may be tested by a simple procedure. Most conveniently, a series of related surfactants are considered, such as a series of alkyl alcohols, condensed with varying amounts of ethylene oxide. A small quantity, for example, ¼ gram of a gram of the putative primary surfactant, is dissolved in several millileters (for example 10 ml) of the oil phase to be dispersed. Where the oil phase to be dispersed is a solution of hydrophobic substance to be dispersed in a solvent, the test should be carried out on that solution. If a clear solution results, a primary surfactant, from the series having a higher HLB (i.e., more ethylene oxide) is selected and the test repeated. When the new surfactant has a sufficiently high HLB, addition of the surfactant will result in a cloudy suspension rather than a clear solution. In this manner, a surfactant (or surfactant mixture) for the oleophilic phase is selected having an HLB not substantially lower than required to render the surfactant soluble in the oil phase.

In practice the surfactants of a series differ by discrete values of HLB. Therefore, in the selection of a surfactant the practical HLB of the first and second members of a series may be too high, and the HLB of the fourth and fifth members of the series will be too low. The third member would be selected, in that case, even though it may not be completely soluble in the oleophilic phase as shown by the simple test.

The hydrophilic-lipophilic balance of a compound is a concept well established in the surfactant field, and generally is used to describe the relative affinities of the hydrophilic and lipophilic moieties which make up the amphiphatic molecule. A substance having a high HLB usually has a relatively strong polar group readily soluble in water and a relatively weak lipophilic group. Typically, such substances are soluble in water but not in oils. Conversely, a substance with a low HLB is usually dominated by a large lipophilic group and is soluble in oils. While there have been some attempts to define an HLB scale on the basis of arbitrary solvents, I have found it more practical for purposes of the present invention to test the HLB of the amphiphatic surfactants to be used with the particular oil and water phases to be emulsified. For example, benzene, if it is used as the oil phase, has a very high affinity for hydrocarbon moieties. To prevent excessive solubilization of the primary surfactant, therefore, a substance with a relatively high HLB would probably be used as the primary surfactant. On the other hand, where an oil phase is used such as a fluorinated solvent, a primary surfactant of a more moderate HLB might be more suitable.

A primary surfactant selected in this manner should be capable of producing a fine, lactescent emulsion. Formation of such an emulsion as described below is generally the first step in the formation of a microemulsion.

Within these guidelines, the selection of a primary surfactant will be well within the skill of the art. It will be evident that the end use of the dispersion of the hydrophobic system in the aqueous system, in some cases, will dictate the type of surfactant employed. For example, if the dispersion is to be ingested by a human being or animal, the surfactant should, of course, be non-toxic and free of other harmful effects.

As previously indicated, in carrying out the present invention the lipophilic phase of the emulsion to be prepared, composed of solvents, substance to be dispersed, and surfactants, is dispersed in the aqueous phase. Microemulsification by the secondary surfactant, as described below, usually will follow only when a good primary lactescent emulsion has been found. Prolonged stability is not necessary in the primary emulsion; however, the droplets of the dispersed phase should be fine enough to impart a milky appearance to the primary emulsion.

The aqueous phase used in the process of this invention is not critical. It may include not only water but a variety of other components depending upon the end use of the product. For example, for purposes of chemical reaction, a catalyst may be provided, and the aqueous phase may contain substances participating in the reaction system. In pharmaceutical preparations the aqueous phase may be buffered. If appropriate, a physiological saline solution may be used. Where detergents, cosmetics or toiletries are to be prepared, the aqueous phase may contain a variety of additional ingredients required to prepare a whole formulation, such as the water-soluble alcohols, and bleaching agents such as sodium hypochlorite or a peroxide. For other purposes, various dyes, colors, dye assistants, perfumes, thickening agents, water-soluble chemical reagents, etc. may be present depending upon the nature of the application to which the microemulsion is applied.

To obtain effective microemulsification, it is important in carrying out this invention to add the oil to the water. Mechanical agitation may be provided sufficient to promote thorough dispersion. In one embodiment of this invention, the oil is added to the water phase in the absence of the secondary surfactant or cosurfactant. In this embodiment, the mixture of oil and water is then shaken or dispersed to produce a lactescent emulsion. Effective microemulsification normally depends upon providing primary emulsifying conditions sufficient and effective to produce a thorough dispersion of the oil in the water. Mixing conditions should be such that transport of the secondary surfactant across the oil-water interface will occur to give rise to the transient conditions required for microemulsification.

As pointed out above, the amount of primary emulsifier dissolved in the oil phase is theoretically sufficient according to equation (1) to result in a dispersion having a droplet size within the microemulsion range (e.g., less than about 1400 angstroms). However, as is well known, a single emulsifier is normally less efficient than a mixed emulsifier system. Therefore, notwithstanding that the amount of primary emulsifier is theoretically sufficient to result in microemulsification in the absence of a secondary emulsifier (as described hereinbelow), the emulsion resulting at this stage of the process does not result in true microemulsification. It should, nevertheless, result in an emulsion in which the dispersed oil droplets of the emulsion are finely distributed throughout the aqueous system.

Where the estimation of the amount of primary surfactant required using the theoretical equation is impractical, a first estimate may be made by employing an amount of primary surfactant equivalent to about 20% by volume of the oil phase to be dispersed. Where the water-oil ratio is large, a greater amount of primary surfactant may be required because of distribution of surfactant between phases.

Following the foregoing, a primary surfactant is selected which will form the best lactescent emulsion if the oil phase is dispersed in water. Thereafter, the initial emulsion is titrated by adding the secondary surfactant to the aqueous system. The amount of secondary surfactant required is that which will convert the lactescent emulsion to a clear microemulsion.

In accordance with this invention, the cosurfactant or secondary surfactant is an amphiphatic substance having a higher HLB than the primary surfactant. Frequently, the secondary surfactant will be soluble in the aqueous phase. Where the primary surfactant has been selected from a series of related substances (such as a series of related ethyleneoxide condensates), the secondary surfactant may, if desired, be selected from the same series and will contain a larger amount of ethylene oxide condensed on the lipophilic moiety than the primary surfactant. It is not necessary, however, that the secondary surfactant bear any chemical relation to the primary surfactant. Indeed, in many cases, the secondary surfactant will not be related to the primary surfactant. For secondary surfactants not only may the common water-soluble surface-active agents (such as those identified above as primary surfactants) be employed but also substances such as short-chain alcohols, for example, pentanol or hexanol.

Where the secondary surfactant is a liquid soluble in water, it will be sufficient to simply add the second surfactant slowly with mild agitation of the primary dispersion. Where the secondary surfactant is a solid, it is frequently preferred to prepare the secondary surfactant as an aqueous concentrate. The concentrate is then added slowly with mild agitation until clarity results to produce the desired microemulsion.

In the alternative, where the amount of secondary surfactant required has been determined from prior experience the process of the present invention may be carried out by dissolving the secondary surfactant in the aqueous phase prior to addition of the oil phase to be dissolved therein. Thereafter, the oil phase containing the dissolved primary surfactant is added to the aqueous phase containing the dissolved secondary surfactant. The system is agitated sufficiently to produce the desired microemulsion.

In either of the foregoing processes, where the solvent is to be removed, after the desired microemulsion has been prepared, the system is gently heated to drive off the solvent and leave behind a stable dispersion of the hydrophobic substance in the aqueous phase. In the alternative, the solvent may be removed by reducing the pressure on the aqueous system.

It is assumed that the addition of anti-flocculating agents (hydrosoluble polymers such as carboxymethylcellulose, polyacryl amide, polyvinyl maleic acid condensates) to the aqueous phase will increase the long-term stability of these frozen in metastable nonequilibrium systems.

The following examples are given by way of illustration only and are not to be considered limiting in any manner.

EXAMPLE 1

The following example illustrates a variety of primary and secondary surfactant systems which were found effective to produce stable clear microemulsions. In each case, the primary surfactant was selected so that it was just barely soluble in the oil phase to be dispersed while the secondary surfactant was selected to be somewhat more hydrophilic than the primary surfactant, and soluble in the water phase.

In each instance, a solution of 2 ml of the specified "oil" was prepared using $\frac{1}{4}$ to 1 ml of the lipo-soluble, or primary, surfactant. The solution was then gently added to water at room temperature and agitated sufficiently to produce a lactescent aqueous emulsion. The amount of water employed varied between 3 and 500 ml. Thereafter, a hydrosoluble, or secondary, surfactant was added to the lactescent emulsion by titration until clarity resulted.

| Oil Phase | Primary Surfactant | Secondary Surfactant |
|---|---|---|
| Light mineral oil | glycerol monooleate | nonylphenol . 9EO |
| Light mineral oil | nonylphenol . 4EO and nonylphenol . 1.5EO in a 1:1 mixture | lauryl alcohol . 7EO |
| Light mineral oil | nonylphenol . 4EO | coco betaine, 30% aqueous solution |
| Benzene | nonylphenol . 1EO | nonylphenol . 15EO |
| Carbon tetrachloride | nonylphenol . 9EO | lauryl alcohol . 7EO |
| 1-pentanol | nonylphenol . 11EO | nonylphenol . 15EO |
| 1-pentanol | nonylphenol . 11EO | lauryl alcohol . 7EO |
| 1-pentanol | nonylphenol . 5EO | nonylphenol . 9.5EO |
| Cl-C-C-C-F* (with Cl, Cl, F and F, F, F) | sorbitan monostearate . 20EA | sorbitan monolaurate . 20EA |
| Cl-C-C-C-F* (with Cl, Cl, F and F, F, F) | sorbitan monostearate . 20EO | nonylphenol . 8-9EO |
| Cl-C-C-C-F* (with Cl, Cl, F and F, F, F) | nonylphenol . 7EO | nonylphenol . 15EO |
| n-hexadecane | nonylphenol . 3EO | nonylphenol . 15EO |
| Carbon tetrachloride | nonylphenol . 9EO | nonylphenol . 15EO |
| Methylene dichloride | nonylphenol . 9EO | nonylphenol . 15EO |
| Light mineral oil | lauryl alcohol . 3EO | lauryl alcohol . 7EO |
| $CCl_4$** | ethylene oxide-propylene oxide block polymer*** | myristyl/lauryl amino betaine |
| $CCl_4$** | nonylphenol . 10–11EO | myristyl/lauryl amino betaine |
| $CCl_4$** | nonylphenol . 10–11EO | lauryl alcohol . 4EO sulfate |

*A solution of tris(hydroxymethyl)aminomethane instead of water was used as the aqueous phase.
**Commercial laundry bleach (5.25% NaOCl) used as the aqueous phase.
***Having a molecular weight of 6,600 and about 70% EO, available commercially as Pluronic F77.

In the foregoing example, silicone, lanolin, polyethylene oxide waxes (such as Carbopol and Carbowax) and fluoroalcohols may generally be substituted for light mineral oil with possible minor modifications in conditions.

With respect to microemulsions of light mineral oil in water, ethoxylated nonylphenol having from 1.5 to 6 moles of ethylene oxide and other glycerol fatty acid partial esters should normally be suitable as a primary surfactant. For this system, it is expected that ethoxylated alkylphenols of 4 to 20 carbon atoms, ethoxylated fatty alcohols and alkyl amino or amido betaines should be suitable as secondary solvents.

EXAMPLE 2

To a solution of 15 ml of trichlorotrifluoroethane containing 3 g of sorbitan monostearate there is added 1 g of 5-(p-methoxyphenyl)-3H-1,2,dithiole-3-thione (a drug sold under the generic name sulfarlem). The mixture is stirred until dissolution occurs. Meanwhile there is prepared an aqueous solution from 20 ml of water containing 3 g of polyoxyethylene sorbitan monolaurate containing 20 mols of ethylene oxide. The first mixture is admixed with the aqueous mixture with gentle stirring until the stable emulsion occurs. Thereafter, the solution is heated gently at about 50°–55° C. for about 1 hour resulting in complete removal of the trichlorotrifluoroethane. The resulting aqueous system is a stable dispersion of 5-(p-methoxyphenyl)-3H-1,2,dithiole-e-thione.

EXAMPLE 3

To 15 ml of n-hexane containing 1.4 g of sorbitan monolaurate there is added 5 g of peanut oil with stirring. After dissolution of the peanut oil, the mixture is added to 20 g of water containing 1.2 g of polyoxyethylene sorbitan monolaurate (containing 20 mols of ethylene oxide). The mixture is stirred resulting in a stable emulsion and thereafter gently heated to about 75° C. for about 1 hour resulting in complete removal of the hexane and a stable transparent aqueous dispersion of peanut oil.

EXAMPLE 4

1.5 g of corn oil is added to a mixture of 8 ml of trichlorotrifluoroethane containing 4 g of polyoxyethylene (20) sorbitan monolaurate. After dissolution of the corn oil, the mixture is added to 20 ml of water containing 1 g of nonylphenol polyethylene glycol ether (9.5 mols of ethylene oxide). The mixture is stirred to form a stable emulsion which is thereafter heated to 50°–55° C. for about 1 hour resulting in complete removal of the trichlorotrifluoroethane. A stable transparent dispersion of corn oil in water results.

EXAMPLE 5

A solvent solution composed of 4 ml of trichlorotrifluoroethane and 1.9 g of polyoxyethylene (20) sorbitan monolaurate is formed. To this solution 1 g of dimethyl polysiloxane is added with agitation until the polysiloxane is dissolved in the solvent. This mixture is then added to an aqueous system composed of 25 ml of a 0.9% saline solution containing 1 g of nonylphenol polyethylene glycol ether (9.5 mols of ethylene oxide).

With stirring, an emulsion is formed and thereafter heated to between about 50°–55° C. for about 1 hour resulting in the removal of the trichlorotrifluoroethane and a stable dispersion of dimethylpolysiloxane in the saline solution.

EXAMPLE 6

A microemulsion composed of carbon tetrachloride dispersed in commercial liquid laundry bleach (5.25% NaOCl) as follows: 0.5 to 1.5 ml of nonylphenol having 10 to 11 ethylene oxide units were dispersed in 2 ml of carbon tetrachloride. The solution was then dispersed in 10 ml of chlorox to form a lactescent emulsion. Upon titration with from 2.5 to 8 ml of a 30% solution of myristyl/lauryl amino betaine, a clear microemulsion resulted. In another example of a carbon tetrachloride-sodium hypochlorite microemulsion, an ethylene oxide-propylene oxide block polymer having 70% ethylene oxide and a molecular weight of 6,600 (commercially available as Pluronic F77) was employed as the primary surfactant. Good results could be obtained using 0.5 to 1.5 ml of the primary solvent in 2 ml of $CCl_4$ and from 5–15 ml of the above-mentioned betaine solution as the secondary solvent with 10 ml of water.

Adding further secondary surfactant will not cloud the system.

EXAMPLE 7

A microemulsion composed of kerosene dispersed in commercial liquid laundry bleach (5.25% Na0) as follows: 2 ml kerosens; 4 ml myristyl dimethyl amine oxide (30% aqueous solution); 10 ml of liquid laundry bleach are mixed together. Upon titration with 1.2 ml t-amyl alcohol or 0.6 ml 3 methyl 3 pentanol, the system becomes clear. It is important that the solvent, primary and secondary surfactants, are not oxidizable by NaOCl. Kerosene, tertiary alcohol and thoroughly oxidized long-chain amine oxide allow the formation of stable systems.

EXAMPLE 8

Example 7 was repeated with the following ingredients:
2 ml kerosene;
0.8 gram decanoic acid;
6 ml KOH 1 normal;
10 ml liquid laundry bleach;
0.7 ml 4 methyl cyclohexanol.

The 4-methyl cyclohexanol and secondary solvent produces a clear microemulsion.

EXAMPLE 9

The procesure of Example 7 was repeated with the following ingredients:
2 ml kerosene;
2 ml Na carboxylated ethylene oxide alcohol;
10 ml liquid laundry bleach;
1.2 ml Ter-amyl or 3 methyl 3 pentanol The 3 methyl-3 pentanol produced a clear microemulsion.

EXAMPLE 10

An essential oil and isopropyl myristate are mixed together (1:2 vol/vol). 2 ml of the oil and 1.5 g of cetyl alcohol·10EO are added to 5 ml of water, and then titrated with 2 ml coconut diethanolamide and 2 ml lauryl betaine (30% aqueous solution). A stable clear gel is obtained. If the volume of water is increased the system becomes less and less viscous until a low viscosity microemulsion is obtained.

EXAMPLE 11

Using the procedure of Example 10, the following were mixed together:
2 ml of essential oil diluted in isopropyl myristate (2 volumes essential oil/1 volume isopropyl myristate)
0.75 grams oleyl alcohol·10 ethylene oxide
10 ml water
10 ml polyethylene glycol monooleate
3 ml lauryl betaine (30% solution)

A clear liquid microemulsion resulted.

In the alternative, the primary emulsifier may be 1 ml of polyethylene glycol monolaurate and the secondary emulsifier may be 3 ml of lauryl betaine (30% solution). In this example, a gel microemulsion may be obtained by using a lower volume of water.

The foregoing examples illustrate several general groups of systems to which the present invention is applicable: 1. The water-immiscible liquid may have a dominant portion of a light mineral oil. A representative oil is n-hexadecane, although obviously mixed oils can be used. The mineral oil can be used either alone or as a solvent for a number of lipophilic substances such as siloxane, lanolin, and hair or skin conditioners, or similar emollients.

Such systems can generally be emulsified by primary surfactants such as the glycerol fatty acid partial esters (such as glycerol monooleates) or ethoxylated alkyl phenols such as nonylphenol having 1.5 to 6 ethylene oxide units. Where the fatty group of the alkyl phenol is increased or decreased in size, the degree of ethoxylation will change to provide the correct HLB as shown by the test described above.

For this system the secondary surfactants are generally ethoxylated alkyl phenols having 4 to 20 carbon atoms, ethoxylated fatty alcohols or alkyl amino or amido betaines having an HLB greater than the HLB of the primary surfactant. Nonylphenol·15EO is one such suitable secondary solvent.

2. The water-immiscible liquid may have a dominant portion of volatile aliphatic petroleum solvents such as pentane or hexane. Such volatile solvents are desirable, for example, when the water-immiscible phase is a solution containing an active ingredient to be emulsified, and from which the solvent is to be removed.

For such systems, a suitable primary solvent would be a sorbitan or sorbitol partial ester, such as sorbitan monolaurate. Because of the solubility relationships no ethoxylation is needed when sorbitan monolaurate is used as the primary surfactant. However, if the lipophilic moiety is increased in size, some small amount of ethylene oxide addition to the ester may be needed.

A suitable secondary surfactant is a sorbitan or sorbitol ester condensed with ethylene oxide, such as sorbitan monolaurate·20EO.

3. The water-immiscible liquid may have a dominant portion of an aromatic solvent such as benzene. Benzene is another good solvent which can be used as a carrier for a variety of lipophilic substances if benzene (or residual traces of it) are acceptable in the final product.

For such systems, nonylphenol·1EO is a suitable solvent. Increasing the size of the alkyl group on the phenol nucleus may require a corresponding increase in the amount of ethoxylation to maintain the desired HLB.

A suitable secondary solvent for this system is nonylphenol having a higher degree of ethoxylation, such as nonylphenol·15EO.

4. A broadly suitable class of water-immiscible liquids are those having dominant portions of a halogenated solvent. These solvents are advantageous for their solubility and non-toxicity, and may be used as carriers for substances such as emollients, etc. If desired, they are easily removed from the finished emulsion. Typically, the common halogenated solvents have from 1 to 3 carbon atoms and are substituted at one or more positions by fluorine or chlorine. The corresponding haloalcohols are also included. Representative solvents are carbon tetrachloride, methylene dichloride, and trichlorotrifluoro ethane.

Suitable primary surfactants for this class of solvents are ethoxylated sorbitan or sorbitol monoesters of $C_{12}$ to $C_{18}$ fatty acids, such as sorbitan monolaurate·20EO and sorbitan monostearate·20EO, and ethoxylated alkyl phenols·7-9EO. As with other applications, the amount of ethoxylation is adjusted to provide the correct HLB. Nonylphenol·9EO is particularly suitable for use with carbon tetrachloride and methylene dichloride. Sorbitan monostearate·20EO works well as a primary surfactant with trichlorotrifluoroethane. Sorbitan monolaurate·20EO is also suitable for this solvent, particularly when another lipophilic substance is dissolved in it.

Secondary surfactants for the halogenated solvent are ethoxylated sorbitan and sorbitol esters of $C_{12}$ to $C_{18}$ fatty acids, such as sorbitan monolaurate·20EO, ethoxylated alkyl phenols such as nonylphenol·8-15EO, and ethoxylated fatty alcohols such as lauryl alcohol·6-10EO. The secondary surfactant is chosen to have a higher HLB than the primary surfactant with which it is used. Nonylphenol·9EO is suitable for use with carbon tetrachloride, and nonylphenol·15EO may be used with methylene dichloride. Nonylphenol·9.5EO is suitable for use with trichlorotrifluoroethane.

5. Still another water-immiscible liquid useful in accordance with the present invention has a dominant portion of 1-pentanol.

A suitable primary surfactant for 1-pentanol is nonylphenol·5-11EO and a suitable secondary surfactant for pentanol is nonylphenol·9.5-15EO and lauryl alcohol·7EO.

6. The aqueous system may contain a salt. Of particular importance are microemulsions having a liquid laundry bleach available commercially as aqueous NaOCl (usually 5.25%). In general, liquid bleaches are within the scope of the present invention and will contain 3% (by weight) or more of soluble oxidizing agents such as alkali metal hypochlorite, hydrogen peroxide, or the alkali metal peroxides. The maximum amount of soluble salt is limited primarily by the solubility limit of the particular salt in question.

Preferably, the surfactants used will not be oxidized or decomposed by the bleach. Preferred surfactants for bleach-containing formulations are:

As the primary surfactant, a $C_{10}$ to $C_{22}$ fatty amine oxide or a $C_{10}$–$C_{22}$ fatty soap. The molecular weight of the primary surfactant will depend on the oil used. The soap, if convenient, may be formed in situ.

As the secondary surfactant, the $C_4$ to $C_{10}$ tertiary alcohols, depending on the nature of the oil.

The principles which have been set forth above are applicable to forming microemulsions employing such liquid bleach. However, the presence of the salt in the liquid phase may alter the solubility relations requiring the selection of somewhat different primary and secondary surfactants. For the purpose of emulsifying carbon-tetrachloride in liquid bleach, the nonylphenols having 10 to 11 ethylene oxide units or an ethylene oxide-propylene oxide block polymer such as the polymers having a molecular weight of 6,000–7,000 containing 60% to 80% (by weight) ethylene oxide are particularly suitable as the primary surfactant. The secondary surfactant may be a fatty amino betaine such as myristyl/lauryl amino betaine or ethoxylated lauryl alcohol such as lauryl alcohol·4EO. Such formulations have demonstrated surprising stability. Stability has been observed from both the standpoint of emulsion stability and from the standpoint of the stability of the dispersed $CCl_4$ and the surfactants to withstand oxidation by the bleaching agents.

Similarly, those skilled in the art will recognize that microemulsions of liquid bleach having other solvents such as light mineral oil or volatile petroleum solvents can be prepared. Care should be exercised in such cases to avoid solvents which would be subject to rapid oxidation by the bleaching agent.

I claim:

1. A method for dispersing a water-immiscible liquid in an aqueous phase as a microemulsion comprising
   (i) selecting a primary surfactant which is an amphiphatic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase;
   (ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;
   (iii) dispersing the solution (ii) of said water-immiscible liquid and primary surfactant into the aqueous phase wherein said liquid is to be dispersed; and
   (iv) providing a secondary surfactant in said aqueous phase which has a higher hydrophilic-lipophilic balance than said primary surfactant, the amount of said secondary surfactant being sufficient to disperse said solution (ii) in the water phase as a microemulsion and having a higher hydrophilic-lipophilic balance than said primary surfactant.

2. A method according to claim 1 wherein said solution (ii) of water-immiscible liquid and primary surfactant is dispersed into the aqueous phase to form a lactescent emulsion, and said secondary surfactant is thereafter added to the lactescent emulsion to form a microemulsion.

3. A method according to claim 1 wherein said primary surfactant is selected from the group consisting of sorbitan esters of fatty acids having 10 to 22 carbon atoms; polyoxyethylene sorbitan esters of $C_{10}$ to $C_{22}$ fatty acids having up to 80% ethylene oxide; polyoxyethylene sorbitol esters of $C_{10}$ to $C_{22}$ fatty acids; polyoxyethylene derivatives of fatty phenols having 6 to 20 carbon atoms in the fatty group, and up to 80% ethylene oxide; fatty amino and amido betaines having 10 to 22 carbon atoms in the fatty group; fatty alcohols of 5 to 16 carbon atoms; polyoxyethylene condensates of $C_{10}$ to $C_{22}$ fatty acids or fatty alcohols having up to 80% ethylene oxide; polyoxyethylene-polyoxypropylene block polymers having 10–80 weight percent ethylene oxide and a molecular weight of 900–16,000; fatty alkyl aryl sulfonates of 6 to 20 carbons in the fatty group; $C_{10}$ to $C_{22}$ fatty acid soaps of an alkali metal or ammonia; $C_{10}$ to $C_{22}$ fatty sulfates; $C_{10}$ to $C_{22}$ fatty sulfonates; $C_{10}$ to $C_{22}$ fatty amine oxides; fatty imidazolines of $C_6$ to $C_{20}$ carbon atoms in the fatty group; fatty amido sulfobetaines having 10 to 22 carbon atoms in the fatty group; fatty ammonium compounds having 10 to 22 carbon atoms; $C_{10}$ to $C_{22}$ fatty morpholine oxides, alkali metal salts of carboxylated ethoxylated $C_{10}$ to $C_{22}$ alcohols, ethylene oxide condensates of $C_{10}$ to $C_{22}$ fatty acid monoesters of glycine, and $C_{10}$ to $C_{22}$ fatty acid mono, and diethanol amides.

4. A method for dispersing a lipophilic substance in an aqueous phase as a microemulsion comprising
(i) dissolving said lipophilic substance in a water-immiscible solvent therefore, forming thereby a water-immiscible solution, said solution containing at least 5% of said lipophilic substance;
(ii) selecting a primary surfactant which is an amphiphatic substance which has a hydrophilic-lipophilic balance not substantially lower than the balance sufficient to render said primary surfactant soluble in said solution and which is capable of forming a lactescent emulsion of said solution (i) in said aqueous phase;
(iii) dissolving said primary surfactant in said solution, the amount of said primary surfactant being sufficient relative to the amount of said solution that upon dispersion of said solution in the water phase as a microemulsion, said primary surfactant will be capable of forming a substantially monomolecular layer of said surfactant around the individual droplets of said microemulsion;
(iv) dispersing said solution (iii) of said lipophilic substance, primary surfactant and water-immiscible solvent into the aqueous phase wherein said substance is to be dispersed; and
(v) providing a secondary surfactant in said aqueous phase which has a higher hydrophilic-lipophilic balance than said primary surfactant, the said secondary surfactant being sufficient to disperse said solution (iii) in said water phase as a microemulsion.

5. A method according to claim 4 wherein said solution (iii) of lipophilic substance, primary surfactant and water-immiscible solvent is dispersed into the aqueous phase to form a lactescent emulsion, and said secondary surfactant is thereafter added to the lactescent emulsion to form a microemulsion.

6. A process according to claim 4 wherein said primary surfactant is selected from the group consisting of sorbitan esters of fatty acids having 10 to 22 carbon atoms; polyoxyethylene sorbitan esters of $C_{10}$ to $C_{22}$ fatty acids having up to 80% ethylene oxide; polyoxyethylene sorbitol esters of $C_{10}$ to $C_{22}$ fatty acids; polyoxyethylene derivatives of fatty phenols having 6 to 20 carbon atoms in the fatty group and up to 80% ethylene oxide; fatty amino and amido betaines having 10 to 22 carbon atoms in the fatty group; fatty alcohols of 5 to 16 carbon atoms; polyoxyethylene condensates of $C_{10}$ to $C_{22}$ fatty acids or fatty alcohols having up to 80% ethylene oxide; polyoxyethylene-polyoxypropylene block polymers having 10–80 weight percent ethylene oxide and a molecular weight of 900–16,000; fatty alkyl aryl sulfonates of 6 to 20 carbons in the fatty group; $C_{10}$ to $C_{22}$ fatty acid soaps of an alkali metal or ammonia; $C_{10}$ to $C_{22}$ fatty sulfates; $C_{10}$ to $C_{22}$ fatty sulfonates; $C_{10}$ to $C_{22}$ fatty amine oxides; fatty imidazolines of $C_6$ to $C_{20}$ carbon atoms in the fatty group; fatty amido sulfobetaines having 10 to 22 carbon atoms in the fatty group; quaternary surfactants such as the fatty ammonium compounds having 10 to 22 carbon atoms; $C_{10}$ to $C_{22}$ fatty morpholine oxides and alkali metal salts of carboxylated ethoxylated $C_{10}$ to $C_{22}$ alcohols, ethylene oxide condensates of $C_{10}$ to $C_{22}$ fatty acid monoesters of glycerine, and the $C_{10}$ to $C_{22}$ mono, and diethanol amides.

7. A method for dispersing a lipophilic substance in an aqueous phase as a microemulsion comprising
(i) dissolving said lipophilic substance in a water-immiscible solvent therefor, forming thereby a water-immiscible solution, said solution containing at least 5% of said lipophilic substance, said water-immiscible solvent being substantially more volatile than water;
(ii) selecting a primary surfactant which is an amphiphatic substance which has a hydrophilic-lipophilic balance not substantially lower than the balance sufficient to render said primary surfactant soluble in said solution and which is capable of forming a lactescent emulsion of said solution (i) in said aqueous phase;
(iii) dissolving said primary surfactant in said solution, the amount of said primary surfactant being sufficient relative to the amount of said solution that upon dispersion of said solution in the water phase as a microemulsion, said primary surfactant will be capable of forming a substantially monomolecular layer of said surfactant around the individual droplets of said microemulsion;
(iv) dispersing said solution (iii) of said lipophilic substance, primary surfactant and water-immiscible solvent into the aqueous phase wherein said substance is to be dispersed; and
(v) providing a secondary surfactant in said aqueous phase which has a higher hydrophilic-lipophilic balance than said primary surfactant, the said secondary surfactant being sufficient to disperse said solution (iii) in said water phase as a microemulsion, and, after dispersion of said solution (iii) in the water phase as a microemulsion, said solution is removed by evaporation.

8. A method according to claim 1 wherein said primary surfactant comprises at least about 20% by volume of said water-immiscible liquid.

9. A process according to claim 4 wherein said primary surfactant comprises at least about 20% by volume of said solution (iii).

10. A method for dispersing a water-immiscible liquid having a dominant portion of a light mineral oil in an aqueous phase as a microemulsion comprising
(i) selecting a primary surfactant which is an amphiphatic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase, said primary surfactant being selected from the group consisting of glycerol fatty acid partial esters and ethoxylated nonylphenol having 3–6 ethylene oxide units per mole;

(ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;

(iii) dispersing the solution (ii) of said water-immiscible liquid and primary surfactant into the aqueous phase wherein said liquid is to be dispersed; and (iv) providing a secondary surfactant in said aqueous phase which has a higher hydrophilic-lipophilic balance than said primary surfactant selected from the group consisting of ethoxylated alkyl phenols, ethoxylated fatty alcohols and alkyl amino or amido betaine, the amount of said secondary surfactant being sufficient to disperse said solution (ii) in the water phase as a microemulsion and having a higher hydrophilic-lipophilic balance than said primary surfactant.

11. A process according to claim 10 wherein said primary surfactant is glycerol monooleate.

12. A process according to claim 10 wherein said primary surfactant is an ethoxylated nonylphenol having 5 to 6 ethylene oxide units per mol.

13. A process according to claim 10 wherein said water-immiscible liquid is a solution of a lipophilic substance in light mineral oil.

14. A method for dispersing a water-immiscible liquid which consists essentially of benzene in an aqueous phase as a microemulsion comprising (i) selecting a primary surfactant which is an amphiphatic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase, said primary surfactant consisting essentially of nonylphenol·1 ethylene oxide;

(ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;

(iii) dispersing the solution (ii) of said water-immiscible liquid and primary surfactant into the aqueous phase wherein said liquid is to be dispersed; and (iv) providing a secondary surfactant in said aqueous phase which has a higher hydrophilic-lipophilic balance than said primary surfactant, said secondary surfactant consisting essentially of nonylphenol·15 EO, the amount of said secondary surfactant being sufficient to disperse said solution (ii) in the water phase as a microemulsion and having a higher hydrophilic-lipophilic balance than said primary surfactant.

15. A method for dispersing a water-immiscible liquid which consists essentially of 1-pentanol in an aqueous phase as a microemulsion comprising (i) selecting a primary surfactant which is an amphiphatic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase, said primary surfactant consisting essentially of ethoxylated nonylphenol having from 5–11 ethylene oxide units;

(ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;

(iii) dispersing the solution (ii) of said water-immiscible liquid and primary surfactant into the aqueous phase wherein said liquid is to be dispersed; and (iv) providing a secondary surfactant in said aqueous phase which has a higher hydrophilic-lipophilic balance than said primary surfactant, said secondary surfactant being selected from the group consisting of ethoxylated phenol having 9.5–15 ethylene oxide units and lauryl alcohol·7 EO, the amount of said secondary surfactant being sufficient to disperse said solution (ii) in the water phase as a microemulsion and having a higher hydrophilic-lipophilic balance than said primary surfactant.

16. A method for dispersing a water-immiscible liquid having a dominant portion of a halogenated solvent in an aqueous phase as a microemulsion comprising (i) selecting a primary surfactant which is an amphiphatic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase, said primary surfactant being selected from the group consisting of ethoxylated sorbitan monoesters of $C_{12}$–$C_{18}$ fatty acids, ethoxylated nonylphenol having 7–9 ethylene oxide units per mole;

(ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;

(iii) dispersing the solution (ii) of said water-immiscible liquid and primary surfactant into the aqueous phase wherein said liquid is to be dispersed; and (iv) providing a secondary surfactant in said aqueous phase which has a higher hydrophilic-lipophilic balance than said primary surfactant, said secondary surfactant being selected from the group consisting of ethoxylated sorbitan monoesters of $C_{12}$–$C_{18}$ fatty acids, ethoxylated sorbitol monoesters of $C_{12}$–$C_{18}$ fatty acids, ethoxylated nonylphenol having 8–15 ethylene oxide units per mole, and lauryl alcohol·6 EO, the amount of said secondary surfactant being sufficient to disperse said solution (ii) in the water phase as a microemulsion and having a higher hydrophilic-lipophilic balance than said primary surfactant.

17. A process according to claim 16 wherein said water-immiscible liquid is carbon tetrachloride, said primary surfactant consists essentially of nonylphenol·9EO, and said secondary surfactant is selected from the group consisting of lauryl alcohol·7EO and nonylphenol·15EO.

18. A process according to claim 16 wherein said halogenated solvent has from 1 to 3 carbon atoms and is substituted in at least one position with chlorine or fluorine.

19. A process according to claim 16 wherein said halogenated solvent is an alcohol having 1 to 3 carbon atoms which is substituted in at least one position with chlorine or fluorine.

20. A process according to claim 10 wherein said water-immiscible liquid consists essentially of n-hexadecane, said primary surfactant consists essentially of nonylphenol·3EO, and said secondary surfactant consists essentially of nonylphenol·15EO.

21. A process according to claim 16 wherein said water-immiscible liquid is a lipophilic substance dissolved in methylene dichloride, said primary surfactant consists essentially of nonylphenol·9EO, and said secondary surfactant consists essentially of nonylphenol·15EO.

22. A method according to claim 7 wherein said water-immiscible solvent is trichlorotrifluoroethane, said primary surfactant consists essentially of sorbitan monostearate·20EO, and said secondary surfactant consists essentially of polyoxyethylene sorbitan monolaurate·20EO.

23. A method according to claim 7 wherein said lipophilic substance is an edible fat, wax or oil, said solvent is n-hexane, said primary surfactant consists essentially of sorbitan monolaurate, and said secondary surfactant consists essentially of sorbitan monolaurate·20EO.

24. A process according to claim 7 wherein said lipophilic substance is an edible fat, wax or oil, said solvent is trichlorofluoroethane, said primary surfactant consists essentially of sorbitan monolaurate·20EO, and said secondary surfactant consists essentially of nonylphenol·9.5EO.

25. A method for dispersing a water-immiscible liquid in an aqueous phase, said aqueous phase having at least 3% of an alkali metal hypochlorite or an alkali-metal peroxide dissolved therein as a microemulsion comprising (i) selecting a primary surfactant which is an amphipathic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase, said primary surfactant being selected from the group consisting of nonylphenol·10-11 EO and ethylene oxide-propylene oxide block polymers having molecular weight of 6,000–7,000 and containing 60–80% ethylene oxide;

(ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;

(iii) dispersing the solution (ii) of said water-immiscible liquid and primary surfactant into the aqueous phase wherein said liquid is to be dispersed; and (iv) providing a secondary surfactant in said aqueous phase which has a higher hydrophilic-lipophilic balance than said primary surfactant, said secondary surfactant being selected from the group consisting of a fatty acid amino betaine and ethoxylated lauryl alcohol, the amount of said secondary surfactant being sufficient to disperse said solution (ii) in the water phase as a microemulsion and having a higher hydrophilic-lipophilic balance than said primary surfactant.

26. A method according to claim 7 wherein said lipophilic substance is a polysiloxane, said solvent is trichlorotrifluoroethane, said primary surfactant consists essentially of sorbitan monolaurate·20EO, and said secondary surfactant consists essentially of nonylphenol·9.5EO.

27. A microemulsion of a water-immiscible liquid dispersed in an aqueous phase having a mixed surfactant system consisting essentially of a primary surfactant and a secondary surfactant, wherein (i) said water-immiscible liquid contains a dominant portion of light mineral oil;

(ii) said primary surfactant is selected from the group consisting of glycerol fatty acid partial esters and ethoxylated nonylphenol having 3 to 6 ethylene oxide units per mol; and (iii) said secondary surfactant is selected from the group consisting of ethoxylated alkylphenols, ethoxylated fatty alcohols and alkylamino or amido betaine.

28. A microemulsion according to claim 27 wherein said primary surfactant is glycerol monooleate.

29. A microemulsion according to claim 27 wherein said primary surfactant is ethoxylated nonylphenol having 5 to 6 ethylene oxide units per mol.

30. A microemulsion according to claim 27 wherein said water-immiscible liquid is a solution of a lipophilic substance in light mineral oil.

31. A microemulsion of benzene dispersed in an aqueous phase having a mixed surfactant system consisting essentially of a primary surfactant and a secondary surfactant, wherein said primary surfactant consists essentially of nonylphenol·1EO, and said secondary surfactant consists essentially of nonylphenol·15EO.

32. A microemulsion according to claim 27 wherein said mineral oil is n-hexadecane, said primary surfactant consists essentially of nonylphenol·3EO, and said secondary surfactant consists essentially of nonylphenol·15EO.

33. A microemulsion of pentanol dispersed in an aqueous phase having a mixed surfactant system consisting essentially of a primary surfactant and a secondary surfactant, wherein said primary surfactant consists essentially of ethoxylated nonylphenol having from 5 to 11 ethylene oxide units and said secondary surfactant is selected from the group consisting of ethoxylated nonylphenol having 9.5 to 15 ethylene oxide units and lauryl alcohol·7EO.

34. A microemulsion of a water-immiscible liquid dispersed in water having a mixed surfactant system consisting essentially of a primary surfactant and a secondary surfactant, wherein (i) said water-immiscible liquid has a dominant portion of a halogenated solvent;

(ii) said primary surfactant is selected from the group consisting of ethoxylated sorbitan monoesters of fatty acids having 12 to 18 carbon atoms, ethoxylated sorbitol monoesters of fatty acids having 12 to 18 carbon atoms, and ethoxylated nonylphenol having 7–9 ethylene oxide units per mol; and (iii) said secondary surfactant is selected from the group consisting of ethoxylated sorbitan monoesters of fatty acids having 12 to 18 carbon atoms, ethoxylated sorbitol monoesters of fatty acids having 12 to 18 carbon atoms, nonylphenol having 8–15 ethylene oxide units per mol, and lauryl alcohol·6–10 EO, said secondary surfactant having a higher hydrophilic-lipophilic balance than said primary surfactant.

35. A microemulsion according to claim 34 wherein said halogenated solvent has from 1 to 3 carbon atoms and is substituted in at least one position with chlorine or fluorine.

36. A microemulsion according to claim 34 wherein said halogenated solvent is an alcohol having 1 to 3 carbon atoms which is substituted in at least one position with chlorine or fluorine.

37. A microemulsion according to claim 34 wherein said solvent is carbon tetrachloride, said primary surfactant consists essentially of nonylphenol·9EO, and said secondary surfactant is selected from the group consisting of lauryl alcohol·7EO and nonylphenol·15EO.

38. A microemulsion according to claim 34 wherein said water-immiscible liquid is a solution of a lipophilic substance in said halogenated solvent.

39. A microemulsion according to claim 38 wherein said water-immiscible liquid is a solution of a lipophilic substance dissolved in methylene dichloride, said primary surfactant consists essentially of nonylphenol·9EO, and said secondary surfactant consists essentially of nonylphenol·15EO.

40. A microemulsion according to claim 34 wherein said water-immiscible liquid has a dominant portion of trichlorotrifluoroethane, said primary surfactant consists essentially of sorbitan monostearate·20EO, and said secondary surfactant consists essentially of polyoxyethylene sorbitan monolaurate·20EO.

41. A microemulsion comprising a dispersion of a water-immiscible liquid in water having a mixed surfactant system consisting essentially of a primary surfactant and a secondary surfactant, wherein said water-immiscible liquid is a solution of an edible fat, wax or oil in n-hexane, said primary surfactant consisting essentially of sorbitan monolaurate, and said secondary surfactant consisting essentially of sorbitan monolaurate·20EO.

42. A microemulsion according to claim 38 wherein said solvent is trichlorofluoroethane, said primary surfactant consists essentially of sorbitan monolaurate·20EO, and said secondary surfactant consists essentially of nonylphenol·9.5EO.

43. A microemulsion according to claim 38 wherein said solvent is trichlorotrifluoroethane, and said lipophilic substance is polysiloxane, said primary surfactant consists essentially of sorbitan monolaurate·20EO, and said secondary surfactant consists essentially of nonylphenol·9.5EO.

44. A microemulsion of a water-immiscible solvent having a dominant portion of carbon tetrachloride in an aqueous phase which has at least 3% of an alkali metal hypochlorite or an alkali metal peroxide dissolved therein, said dispersion having a mixed surfactant system consisting essentially of a primary surfactant and a secondary surfactant, wherein said primary surfactant is selected from the group consisting of nonylphenol·10–11EO and ethylene oxidepropylene oxide block polymers having a molecular weight of 6,000–7,000 and containing 60–80% ethylene oxide; and wherein said secondary surfactant is selected from the group consisting of a fatty amino betaine and ethoxylated lauryl alcohol.

45. A method for dispersing a water-immiscible liquid in an aqueous phase having at least 3% of an alkali metal hypochlorite, hydrogen peroxide or an alkali metal peroxide dissolved therein as a microemulsion comprising (i) selecting a primary surfactant which is an amphiphatic substance which has a hydrophilic-lipophilic balance not substantially lower than the balance sufficient to render said primary surfactant soluble in said water-immiscible liquid, and which is capable of forming a lactescent emulsion of said water-immiscible liquid dispersed in said aqueous phase, said primary surfactant being selected from the group consisting of $C_{10}$–$C_{22}$ fatty amine oxides, and a $C_{10}$–$C_{22}$ fatty acid soap;

(ii) dissolving said primary surfactant in said water-immiscible liquid, the amount of said primary surfactant being sufficient relative to the amount of said water-immiscible liquid that upon dispersion of said water-immiscible liquid in the water phase as a microemulsion, said primary surfactant will be capable of forming a substantially monomolecular layer of surfactant around the individual droplets of said microemulsion;

(iii) dispersing the solution (ii) of said water-immiscible liquid and primary surfactant into the aqueous phase wherein said liquid is to be dispersed; and (iv) providing a secondary surfactant in said aqueous phase which has a higher hydrophilic-lipophilic balance than said primary surfactant, said secondary surfactant being a $C_4$–$C_{10}$ tertiary alcohol, the amount of said secondary surfactant being sufficient to disperse said solution (ii) in the water phase as a microemulsion and having a higher hydrophilic-lipophilic balance than said primary surfactant.

46. A microemulsion according to claim 27, wherein (a) said aqueous phase has at least 3% of an alkali metal hypochlorite, hydrogen peroxide or an alkali metal peroxide;

(b) said primary surfactant is selected from the group consisting of a $C_{10}$ to $C_{22}$ fatty amine oxide or a $C_{10}$ to $C_{22}$ fatty acid soap; and (c) the secondary surfactant is a $C_4$ to $C_{10}$ tertiary alcohol.

* * * * *

UNITED STATES PATENT OFFICE
CERTIFICATE OF CORRECTION

Patent No. 4,146,499           Dated  March 27, 1979

Inventor(s)    Henri L. Rosano

It is certified that error appears in the above-identified patent and that said Letters Patent are hereby corrected as shown below:

Col. 6, line 62, "groups" should read --group--;
Col. 8, line 4, "1/4 gram" should read --1/2 gram--;
Col. 11, line 1, "3 and .500" should read --3 and 500--;
Col. 11, table, 12th line of second column and 11th line of third column, ".20EA" should read -- .20EO--;
Col. 11, first footnote following table, "queous" should read --aqueous--; and
Col. 14, line 22, "1. The water- ..." should start a new paragraph.

Signed and Sealed this

Fourteenth Day of October 1980

[SEAL]

Attest:

SIDNEY A. DIAMOND

Attesting Officer    Commissioner of Patents and Trademarks